United States Patent [19]

Bouchard et al.

[11] Patent Number: 5,606,083

[45] Date of Patent: Feb. 25, 1997

[54] PROCESS FOR THE PREPARATION OF TAXANE DERIVATIVES, NEW DERIVATIVES THUS OBTAINED AND THE COMPOSITIONS WHICH CONTAIN THEM

[75] Inventors: Herve Bouchard, Ivry Sur Seine; Jean-Dominique Bourzat, Vincennes; Alain Commercon, Vitry-Sur-Seine, all of France

[73] Assignee: Rhone-Poulenc Rorer S.A., Antony, France

[21] Appl. No.: 424,512

[22] PCT Filed: Nov. 22, 1993

[86] PCT No.: PCT/FR93/01145

§ 371 Date: May 23, 1995

§ 102(e) Date: May 23, 1995

[87] PCT Pub. No.: WO94/12484

PCT Pub. Date: Jun. 9, 1994

[30] Foreign Application Priority Data

Nov. 23, 1992 [FR] France ................................. 92 14023

[51] Int. Cl.⁶ .................................................. C07D 305/14
[52] U.S. Cl. .................................... 549/510; 549/511
[58] Field of Search ................................. 549/510, 511

[56] References Cited

U.S. PATENT DOCUMENTS

| 4,814,470 | 3/1989 | Colin et al. | 514/449 |
| 5,229,526 | 7/1993 | Holton | 549/213 |

FOREIGN PATENT DOCUMENTS 0253738  1/1988  European Pat. Off. .

OTHER PUBLICATIONS

Commergan et al, "Tetrahedron Letters", 33(36), pp. 5185–5188, 1992.

Primary Examiner—Ba K. Trinh
Attorney, Agent, or Firm—Finnegan, Henderson, Farabow, Garrett & Dunner, L.L.P.

[57] ABSTRACT

This invention relates to a method for the preparation of taxane derivatives having the formula (I) and pharmaceutical compositions which contain the derivatives thus obtained. In formula (I), R is hydrogen or acetyl, $R_1$ is benzoyl or $R_2$—O—CO wherein $R_2$ is alkyl, alkenyl, alkynyl, cycloalkyl, cycloalkenyl, bicycloalkyl, phenyl or heterocyclyl and Het is a 5-membered optionally substituted aromatic heterocycle (thiophene, tiazole, furan, pyrrole, imidazole, oxazole, isoxazole, pyrazole). The products of formula (I) have remarkable antitumor and antileukemia properties.

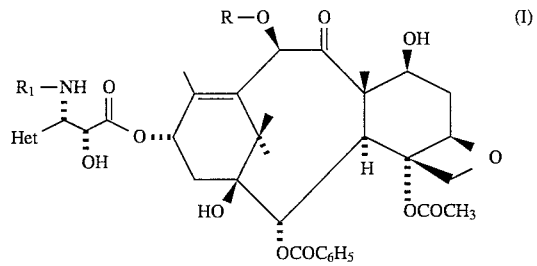

25 Claims, No Drawings

PROCESS FOR THE PREPARATION OF TAXANE DERIVATIVES, NEW DERIVATIVES THUS OBTAINED AND THE COMPOSITIONS WHICH CONTAIN THEM

DESCRIPTION OF THE INVENTION

This application is a 371 of PCT/FR93/01145, dated Nov. 22, 1993.

The present invention relates to the preparation of taxane derivatives of general formula:

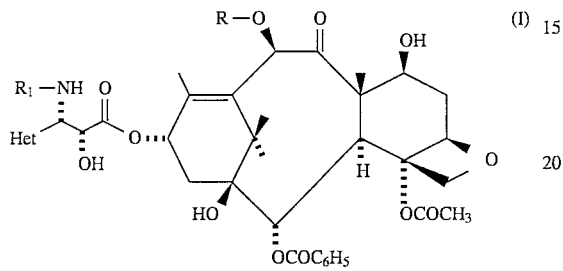

to the new products thus obtained and to the pharmaceutical compositions which contain them.

In the general formula (I), R represents a hydrogen atom or an acetyl radical, $R_1$ represents a benzoyl radical or a radical $R^2$—O—CO— in which $R_2$ represents an alkyl, alkenyl, alkynyl, cycloalkyl, cycloalkenyl, bicycloalkyl, phenyl or heterocyclyl radical, and Het represents an optionally substituted aromatic heterocyclyl radical having 5 members and containing one or a number of heteroatoms, which are identical or different, chosen from nitrogen, oxygen and sulphur.

More particularly, the present invention relates to the preparation of the products of general formula (I) in which:

R represents a hydrogen atom or an acetyl radical, $R_1$ represents a benzoyl radical or a radical $R_2$—O—CO in which $R^2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by one or a number of substituents, which are identical or different, chosen from the halogen atoms and the hydroxyl radical, alkoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, nitro radical, carboxyl radical or alkoxycarbonyl radical, the alkyl part of which contains 1 to 4 carbon atoms, or a phenyl radical, optionally substituted by one or a number of radicals, which are identical or different, chosen from the alkyl radicals containing 1 to 4 carbon atoms or the alkoxy radicals containing 1 to 4 carbon atoms, or a saturated or unsaturated nitrogen-containing heterocyclyl radical containing 5 or 6 members, optionally substituted by one or a number of alkyl radicals containing 1 to 4 carbon atoms, it being understood that the cycloalkyl, cycloalkenyl or bicycloalkyl radicals may optionally be substituted by one or a number of alkyl radicals containing 1 to 4 carbon atoms, and Het represents an aromatic heterocyclic radical having 5 members and containing one or a number of atoms, which are identical or different, chosen from the nitrogen, oxygen or sulphur atoms, such as thiophene, thiazole, furan, pyrrole, imidazole, isoxazole or pyrazole, optionally substituted by one or a number of substituents, which are identical or different, chosen from the halogen atoms (fluorine, chlorine) and the alkyl, containing 1 to 4 carbon atoms, aryl, containing 6 to 10 carbon atoms, alkoxy, containing 1 to 4 carbon atoms, aryloxy, containing 6 to 10 carbon atoms, amino, alkylamino, containing 1 to 4 carbon atoms, dialkylamino, each alkyl part of which contains 1 to 4 carbon atoms, acylamino, the acyl part of which contains 1 to 4 carbon atoms, alkoxycarbonylamino, containing 1 to 4 carbon atoms, acyl, containing 1 to 4 carbon atoms, arylcarbonyl, the aryl part of which contains 6 to 10 carbon atoms, cyano, nitro, hydroxyl, carboxyl, carbamoyl, alkylcarbamoyl, the alkyl part of which contains 1 to 4 carbon atoms, dialkylcarbamoyl, each alkyl part of which contains 1 to 4 carbon atoms, or alkoxycarbonyl, the alkoxy part of which contains 1 to 4 carbon atoms, radicals.

The preparation of the products of general formula (I) in which R represents a hydrogen atom or an acetyl radical, $R_1$ represents a benzoyl radical or a radical $R_2$—O—CO— in which $R^2$ represents a t-butyl radical and Het represents a 2- or 3-thienyl or 2- or 3-furyl radical is very particularly advantageous.

According to the present invention, the derivatives of general formula (I) can be obtained from a product of general formula:

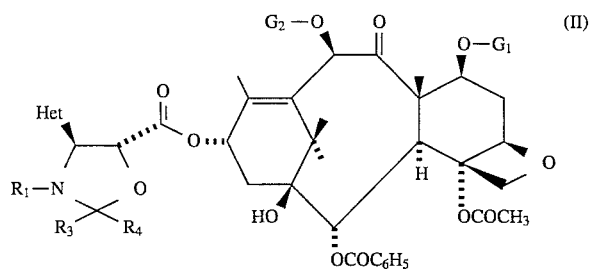

in which Het and $R_1$ are defined as above, $G_1$ represents a protective group of the hydroxyl functional group and $G_2$ represents an acetyl radical or a protective group of the hydroxyl functional group, and $R_3$ and $R_4$, which are identical or different, represent a hyrogen atom or an alkyl radical containing 1 to 4 carbon atoms, or an aralkyl radical, the alkyl part of which contains 1 to 4 carbon atoms and the aryl part preferably represents a phenyl radical optionally substituted by one or a number of alkoxy radicals containing 1 to 4 carbon atoms, or an aryl radical preferably representing a phenyl radical optionally substituted by one or a number of alkoxy radicals containing 1 to 4 carbon atoms, or else $R_3$ represents an alkoxy radical containing 1 to 4 carbon atoms or a trihalomethyl radical such as trichloromethyl or a phenyl radical substituted by a trihalomethyl radical such as trichloromethyl and $R_4$ represents a hydrogen atom, or else $R_3$ and $R^4$ form, together with the carbon atom to which they are bonded, a ring having 4 to 7 members, the reaction being carried out, depending on the meanings of $R^3$ and $R_4$, in the following way:

1) when $R^3$ represents a hydrogen atom or an alkoxy radical or an optionally substituted aryl radical and $R_4$ represents a hydrogen atom, the product of general formula (II) is treated in acid medium to produce a product of general formula:

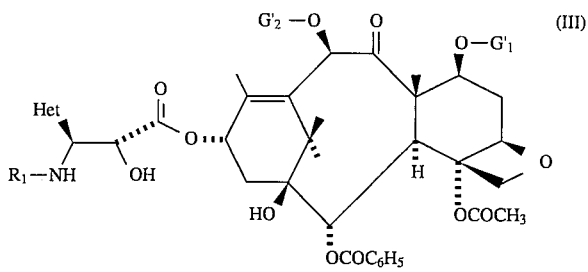

in which Het and $R_1$ are defined as above, $G'_1$ represents a hydrogen atom or a protective group of the hydroxyl functional group and $G'_2$ represents a hydrogen atom or an acetyl radical or a protective group of the hydroxyl functional group, the $G'_1$ and $G'_2$ protective groups of which are, if necessary, replaced by hydrogen atoms to produce a product of general formula (I).

The deprotection of the side chain of the product of general formula (II) can be carried out in the presence of an inorganic acid (hydrochloric acid, sulphuric acid) or organic acid (acetic acid, methanesulphonic acid, trifluoromethanesulphonic acid, p-toluenesulphonic acid), used alone or as a mixture, the reaction being carried out in an organic solvent chosen from alcohols (methanol, ethanol, isopropanol), ethers (tetrahydrofuran, diisopropyl ether, methyl t-butyl ether), esters (ethyl acetate, isopropyl acetate, n-butyl acetate), aliphatic hydrocarbons (pentane, hexane, heptane), halogenated aliphatic hydrocarbons (dichloromethane, 1,2-dichloroethane), aromatic hydrocarbons (benzene, toluene, xylenes) and nitriles (acetonitrile) at a temperature between −10° and 60° C., preferably between 15° and 30° C. The inorganic acid can be used in a catalytic or stoichiometric amount or in excess.

The deprotection can also be carried out under oxidizing conditions by using, for example, cerium (IV) ammonium nitrate in an acetonitrile/water mixture or 2,3-dichloro-5,6-dicyano-1,4-benzoquinone in water.

The deprotection can also be carried out under reducing conditions, for example by hydrogenolysis in the presence of a catalyst.

The $G_1$ and $G_2$, and $G'_1$ and $G'_2$, radicals, when they represent a protective group of the hydroxyl functional group, are preferably 2,2,2-trichloroethoxycarbonyl or 2-(2-(trichloromethyl)propoxy)carbonyl radicals or trialkylsilyl, dialkylarylsilyl, alkyldiarylsilyl or triarylsilyl radicals in which the alkyl parts contain 1 to 4 carbon atoms and the aryl parts are preferably phenyl radicals.

When, in the general formula (II), the $G_1$ and optionally $G_2$ protective groups represent a silylated radical, their replacement by hydrogen atoms is carried out simultaneously with the deprotection of the side chain.

The replacement by hydrogen atoms, in the product of general formula (III), of the protective groups $G'_1$ and $G'_2$ representing a 2,2,2-trichloroethoxycarbonyl or 2-(2-(trichloromethyl)propoxy)carbonyl radical is carried out with zinc, optionally in combination with copper, in the presence of acetic acid at a temperature between 20° and 60° C. or by means of an inorganic or organic acid such as hydrochloric acid or acetic acid in solution in an aliphatic alcohol containing 1 to 3 carbon atoms or in an aliphatic ester such as ethyl acetate, isopropyl acetate or n-butyl acetate in the presence of zinc, optionally in combination with copper, 2) when $R_3$ and $R_4$, which are identical or different, represent an alkyl radical containing 1 to 4 carbon atoms, or an aralkyl radical, in which the alkyl part contains 1 to 4 carbon atoms and the aryl part is preferably an optionally substituted phenyl radical, or an aryl radical, preferably an optionally substituted phenyl radical, or else $R^3$ represents a trihalomethyl radical or a phenyl radical substituted by a trihalomethyl radical and $R^4$ represents a hydrogen atom, or else $R_3$ and $R_4$ form, together with the carbon atom to which they are bonded, a ring having 4 to 7 members, the product of general formula (II) is converted to the product of general formula:

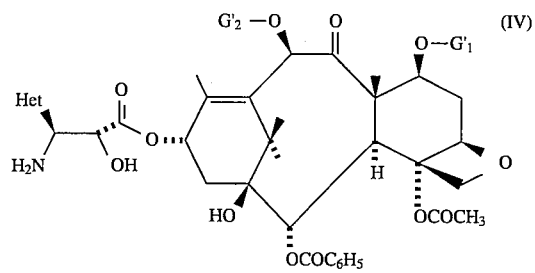

in which Het is defined as above, $G'_1$ represents a hydrogen atom or a protective group of the hydroxyl functional group and $G'_2$ represents a hydrogen atom or an acetyl radical or a protective group of the hydroxyl functional group, which is acylated by means of benzoyl chloride or of a reactive derivative of general formula:

$$R_2\text{—O—CO—X} \qquad (V)$$

in which $R^2$ is defined as above and X represents a halogen (fluorine, chlorine) atom or an —O—$R_2$ or —O—CO—O—$R^2$ residue, to produce a product of general formula (III), the $G'_1$ and optionally $G'_2$ protective groups of which are replaced, if necessary, by hydrogen atoms to produce a product of general formula (I).

The products of general formula (IV), in which $G'_1$ represents a protective group of the hydroxyl functional group chosen from the 2,2,2-trichloroethoxycarbonyl and 2-(2-(trichloromethyl)propoxy)carbonyl radicals and $G'_2$ represents an acetyl radical or a protective group of the hydroxyl functional group chosen from the 2,2,2-trichloroethoxycarbonyl and 2-(2-(trichloromethyl)propoxy)carbonyl radicals, can be obtained by treating a product of general formula (II), in which Het, $R_1$, $G_1$ and $G_2$ are defined as above, $R_3$ and $R_4$, which are identical or different, represent an alkyl, aralkyl or aryl radical, or else $R^3$ and $R^4$ form, together with the carbon atom to which they are bonded, a ring having 4 to 7 members, with an inorganic acid (hydrochloric acid, sulphuric acid) or organic acid (formic acid) optionally in an alcohol containing 1 to 3 carbon atoms (methanol, ethanol, ispropanol) at a temperature between 0° and 50° C. Formic acid at a temperature in the region of 20° C. is preferably used.

The products of general formula (IV), in which $G'_1$ represents a hydrogen atom and $G'_2$ represents an acetyl radical, can be obtained by treating a product of general formula (II), in which $G_1$ represents a silylated radical and $G_2$ represents an acetyl radical, $R_3$ and $R_4$, which are identical or different, represent an alkyl, aralkyl or aryl radical, or else $R_3$ and $R_4$ form, together with the carbon atom to which they are bonded, a ring having 4 to 7 members, with an inorganic acid (hydrochloric acid, sulphuric acid, hydrofluoric acid) or organic acid (formic acid, acetic acid, methanesulphonic acid, trifluoromethanesulphonic acid, p-toluenesulphonic acid), used alone or as a mixture, the reaction being carried out in an organic solvent chosen from alcohols, ethers, esters, aliphatic hydrocarbons, halogenated aliphatic hydrocarbons, aromatic hydrocarbons or nitriles at a temperature between −10° and 60° C.

The products of general formula (IV) in which $G'_1$ represents a hydrogen atom and $G'_2$ represents a hydrogen atom or an acetyl radical can be obtained by treating a product of general formula (II), in which $G_1$ represents a protective group chosen from the 2,2,2-trichloroethoxycarbonyl or 2-(2-(trichloromethyl)propoxy)carbonyl radicals, $G_2$ represents an acetyl radical or a protective group chosen from the 2,2,2-trichloroethoxycarbonyl or 2-(2-(trichloromethyl)propoxy)carbonyl radicals, $R_3$ represents a trihalomethyl radical or phenyl radical substituted by a trihalomethyl radical and $R_4$ represents a hydrogen atom, with zinc, optionally in combination with copper, in the presence of acetic acid at a temperature between 30° and 60° C. or by means of an inorganic or organic acid such as hydrochloric acid or acetic acid in solution in an aliphatic alcohol containing 1 to 3 carbon atoms (methanol, ethanol, propanol, isopropanol) or in an aliphatic ester (ethyl acetate, isopropyl acetate or n-butyl acetate) in the presence of zinc, optionally in combination with some copper.

The acylation of the product of general formula (IV) by means of benzoyl chloride or of a reactive derivative of general formula (V) is carried out in an inert organic solvent chosen from esters such as ethyl acetate, sopropyl acetate or n-butyl acetate and halogenated aliphatic hydrocarbons such as dichloromethane or 1,2-dichloroethane in the presence of an inorganic base such as sodium bicarbonate or of an organic base such as triethylamine. The reaction is carried out at a temperature between 0° and 50° C., preferably in the region of 20° C.

The optional replacement by hydrogen atoms of the $G'_1$ and $G'_2$ protective groups of the product of general formula (III), when they represent a 2,2,2-trichloroethoxycarbonyl or 2-(2-(trichloromethyl)propoxy)carbonyl radical, is generally carried out by treatment with zinc, optionally in combination with copper, in the presence of acetic acid at a temperature between 30° and 60° C. or by means of an inorganic or organic acid such as hydrochloric acid or acetic acid in solution in an aliphatic alcohol containing 1 to 3 carbon atoms (methanol, ethanol, isopropanol) or in an aliphatic ester (ethyl acetate, isopropyl acetate, n-butyl acetate) in the presence of zinc, optionally in combination with copper.

The products of general formula (II) can be obtained by esterification of protected 10-deacetylbaccatin III or baccatin III of general formula:

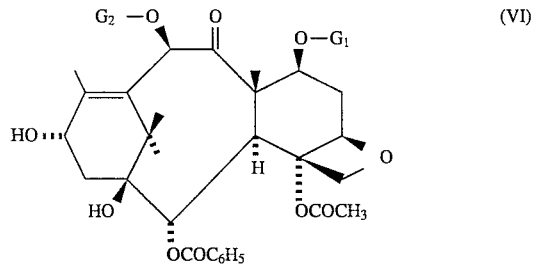

in which $G_1$ and $G_2$ are defined as above, by means of an acid of general formula:

in which Het, $R_1$, $R_3$ and $R_4$ are defined as above, or of a derivative of this acid.

The esterification by means of an acid of general formula (VII) can be carried out in the presence of a condensation agent (carbodiimide, reactive carbonate) and of an activating agent (aminopyridine) in an organic solvent (ether, ester, ketones, nitriles, aliphatic hydrocarbons, halogenated aliphatic hydrocarbons, aromatic hydrocarbons) at a temperature between −10° and 90° C.

The esterification can also be carried out by using the acid of general formula (VII) in the anhydride form, the reaction being carried out in the presence of an activating agent (aminopyridine) in an organic solvent (ethers, esters, ketones, nitriles, aliphatic hydrocarbons, halogenated aliphatic hydrocarbons, aromatic hydrocarbons) at a temperature between 0° and 90° C.

The esterification can also be carried out by using the acid of general formula (VII) in the halide form or in the form of an anhydride with an aliphatic or aromatic acid, optionally prepared in situ, in the presence of a base (tertiary aliphatic amine), the reaction being carried out in an organic solvent (ethers, esters, ketones, nitriles, aliphatic hydrocarbons, halogenated aliphatic hydrocarbons, aromatic hydrocarbons) at a temperature between 0° and 80° C.

The acid of general formula (VII) can be obtained by saponification of an ester of general formula:

in which Het, $R_1$, $R_3$ and $R_4$ are as defined as above and $R_5$ represents an alkyl radical containing 1 to 4 carbon atoms, optionally substituted by a phenyl radical.

Generally, the saponification is carried out by means of an inorganic base (alkali metal hydroxide, carbonate or bicarbonate) in water/alcohol medium (methanol/water) at a temperature between 10° and 40° C.

The ester of general formula (VIII) can be obtained by reacting a product of general formula:

in which $R_3$ and $R^4$ are as defined above, in the form of a dialkyl acetal or of an enol alkyl ether, with an ester of general formula:

in which Het, $R_1$ and $R_5$ are defined as above, the reaction being carried out in an inert organic solvent (aromatic hydrocarbon) in the presence of a strong inorganic acid (sulphuric acid) or strong organic acid (p-toluenesulphonic acid, optionally in the form of the pyridinium salt) at a temperature between 0° C. and the boiling temperature of the reaction mixture.

The ester of general formula (X) can be obtained by reacting a product of general formula (V) with an ester of general formula:

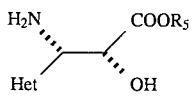 (XI)

in which Het and $R_s$ are as defined above, the reaction being carried out in an organic solvent (ester, halogenated aliphatic hydrocarbon) in the presence of an inorganic or organic base at a temperature between 0° and 50° C.

The product of general formula (XI), in which Het preferably represents a sulphur-containing heterocycle, can be obtained by reduction of an azide of general formula:

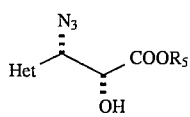 (XII)

in which Het and $R_5$ are defined as above, by means of hydrogen in the presence of a catalyst such as palladium-on-charcoal, the reaction being carried out in an organic solvent (ester).

The product of general formula (XII) can be obtained by reacting an azide such as trimethylsilyl azide in the presence of zinc chloride or alkali metal (sodium, potassium, lithium) azide in water/organic medium (water/tetrahydrofuran) at a temperature between 20° C. and the boiling temperature of the reaction mixture with an epoxide of general formula:

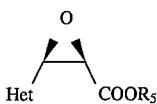 (XIII)

in which Het and $R_5$ are defined as above, optionally prepared in situ.

The epoxide of general formula (XIII) can be obtained, optionally in situ, by dehydrohalogenation of a product of general formula:

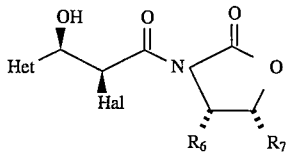 (XIV)

in which Het is defined as above, Hal represents a halogen atom, preferably a bromine atom, and $R_6$ and $R_7$, which are identical or different, represent a hydrogen atom or an alkyl radical containing 1 to 4 carbon atoms or a phenyl radical, at least one being an alkyl radical or a phenyl radical, by means of an alkali metal alkoxide, optionally prepared in situ, in an inert organic solvent such as tetrahydrofuran at a temperature between −80° C. and 25° C.

The product of general formula (XIV) can be obtained by reacting an aldehyde of general formula:

Het-CHO (XV)

in which Het is defined as above, with a halide of general formula:

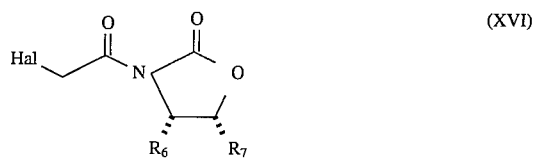 (XVI)

in which Hal, $R_6$ and $R_7$ are defined as above, anionized beforehand.

Generally, the reaction is carried out in an inert organic solvent chosen from ethers (ethyl ether) and halogenated aliphatic hydrocarbons (methylene chloride) at a temperature between −80° and 25° C., in the presence of a tertiary amine (triethylamine) and of an enolization agent (di-n-butylboron triflate).

The product of general formula (XVI) can be obtained by reacting a halide of a haloacetic acid, preferably the bromide of bromoacetic acid, with the corresponding oxazolidinone.

The product of general formula (XI) in which Het preferably represents an oxygen-containing heterocycle can be obtained by hydrogenolysis of a product of general formula:

 (XVII)

in which Het and $R_5$ are as defined above and Ph represents an optionally substituted phenyl radical.

The hydrogenolysis is generally carried out using hydrogen in the presence of a catalyst. More particularly, a palladium-on-charcoal containing 1 to 10% by weight of palladium or palladium dihydroxide containing 20% by weight of palladium is used as catalyst.

The hydrogenolysis is carried out in an organic solvent or in a mixture of organic solvents. It is advantageous to carry out the reaction in acetic acid, optionally in combination with an aliphatic alcohol containing 1 to 4 carbon atoms, such as an acetic acid/methanol mixture at a temperature between 20° and 80° C.

The hydrogen required for the hydrogenolysis can also be provided by a compound which releases hydrogen by chemical reaction or by thermal decomposition (ammonium formate). It is advantageous to carry out the reaction under a hydrogen pressure between 1 and 50 bar.

The product of general formula (XVII) can be obtained by hydrolysis or alcoholysis of a product of general formula:

 (XVIII)

in which Het and Ph are defined as above. It is particularly advantageous to carry out an alcoholysis using an alcohol of formula $R_5$—OH in which $R_5$ is defined as above, the reaction being carried out in an acid medium.

The alcoholysis is preferably carried out using methanol in the presence of a strong inorganic acid such as hydrochloric acid at a temperature in the region of the reflux temperature of the reaction mixture.

The product of general formula (XVIII) can be obtained by saponification of an ester of general formula:

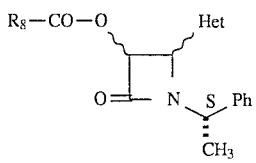 (XIX)

in which Het and Ph are defined as above and $R_8$ represents an alkyl, phenylalkyl or phenyl radical, followed by the separation of the 3R,4S diastereoisomer of general formula (XVIII) from the other diastereoisomers.

The saponification is generally carried out using an inorganic or organic base such as aqueous ammonia, lithium hydroxide, sodium hydroxide or potassium hydroxide in a suitable solvent such as a methanol/water or tetrahydrofuran/water mixture at a temperture between −10° C. and 20° C.

The separation of the 3R,4S diastereoisomer can be carried out by selective crystallization from a suitable organic solvent such as ethyl acetate.

The product of general formula (XIX) can be obtained by cycloaddition of an imine of general formula:

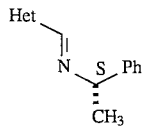 (XX)

in which Het and Ph are defined as above, to an acid halide of general formula:

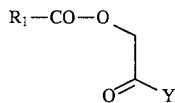 (XXI)

in which $R_1$ is as defined as above and Y represents a halogen atom such as a bromine or chlorine atom.

The reaction is generally carried out at a temperature between 0° and 50° C. in the presence of a base chosen from tertiary aliphatic amines (triethylamine) or pyridine in an organic solvent chosen from optionally halogenated aliphatic hydrocarbons (methylene chloride, chloroform) and aromatic hydrocarbons (benzene, toluene, xylenes).

The product of general formula (XX) can be obtained under conditions analogous to those described by M. Furukawa et al., Chem. Pharm. Bull., 25 (1), 181–84 (1977).

Protected 10-deacetylbaccatin III or baccatin III of general formula (VI) can be obtained under the conditions described in European Patents EP-0,336,840 and EP-0,336,841.

The derivatives of general formula (I) can also be obtained by esterification of protected 10-deacetylbaccatin III or baccatin III of general formula (VI) by means of an acid of general formula:

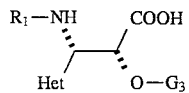 (XXII)

in which Het and $R_1$ are defined as above and $G_3$ represents a protective group of the hydroxyl functional group chosen from the methoxymethyl, 1-ethoxyethyl, benzyloxymethyl, (β-trimethylsilyloxy)methyl, tetrahydropyranyl, 2,2,2-trichloroethoxymethyl, 2,2,2-trichloroethoxycarbonyl or $CH_2$-Ph radicals, in which Ph represents a phenyl radical optionally substituted by one or a number of atoms or radicals, which are identical or different, chosen from halo- gen atoms and alkyl radicals containing 1 to 4 carbon atoms or alkoxy radicals containing 1 to 4 carbon atoms, or of an activated derivative of this acid, to produce a product of general formula:

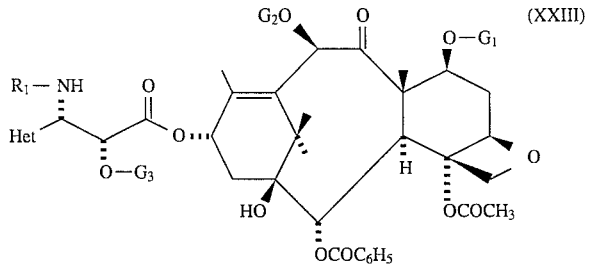 (XXIII)

in which Het, $R_1$, $G_1$, $G_2$ and $G_3$ are defined as above, followed by replacement of the $G_1$, $G_2$ and $G_3$ protective groups by hydrogen atoms to produce a product of general formula (I).

The esterification can be carried out under the conditions described above for the esterification of protected 10-deacetylbaccatin III or baccatin III of general formula (VI) by means of an acid of general formula (VII).

The replacement of the $G_1$, $G_2$ and $G_3$ protective groups of the product of general formula (XXIII) by hydrogen atoms is carried out by treatment with zinc, optionally in combination with copper, in the presence of acetic acid at a temperature between 30° and 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc, optionally in combination with copper, when $G_2$, $G_2$ and/or $G_3$ represent a 2,2,2-trichloroethoxycarbonyl or 2-(2-(trichloromethyl)propoxy)carbonyl radical, or by treatment in acid medium such as, for example, hydrochloric acid in solution in an aliphatic alcohol containing 1 to 3 carbon atoms (methanol, ethanol, propanol, isopropanol) or aqueous hydrofluoric acid at a temperature between 0° and 40° C. when $G_1$, $G_2$ and/or $G_3$ represent a silylated radical. When $G_3$ represents a —$CH_2$—Ph group, it is necessary to replace this protective group by a hydrogen atom by hydrogenolysis in the presence of a catalyst, after having replaced the $G_1$ and $G_2$ protective groups by hydrogen atoms under the conditions described above.

The acid of general formula (XXII) can be obtained by saponification of an ester of general formula:

 (XXIV)

in which Het, $R_1$, $R_5$ and $G_3$ are defined as above.

The saponification is generally carried out using an inorganic base (alkali metal hydroxide, carbonate or bicarbonate) in water/alcohol medium (methanol/water) at a temperature betwewen 10° and 40° C.

The ester of general formula (XXIV) can be obtained according to the usual methods for the preparation of ethers, and more particularly according to the processes described by J-N. Denis et al., J. Org. Chem., 51, 46–50 (1986) from a product of general formula (X).

The products of general formula (I) obtained by the use of the processes according to the invention can be purified according to known methods such as crystallization or chromatography.

The present invention also relates to new taxane derivatives of general formula:

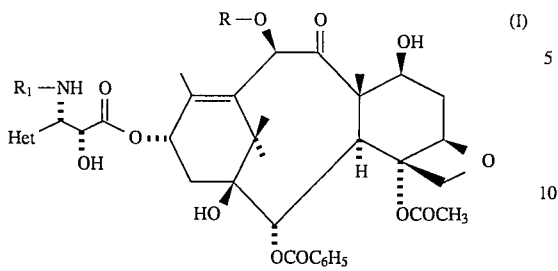

and to the pharmaceutical compositions which contain them.

In the general formula (I),

R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or heterocyclyl radical, and Het represents an optionally substituted aromatic heterocyclyl radical having 5 members and containing one or a number of identical or different heteroatoms chosen from nitrogen, oxygen and sulphur with the exception of Het representing a 2-furyl or 2-thienyl radical when $R_1$ represents a benzoyl radical or when $R_2$ represents an alkyl radical containing 1 to 6 carbon atoms, the corresponding products being described in EP-A-0, 534,708.

More particularly, the present invention relates to the products of general formula (I) in which:

R represents a hydrogen atom or an acetyl radical, $R_1$ represents a benzoyl radical or a radical $R_2$—O—CO in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by one or a number of substituents, which are identical or different, chosen from the halogen atoms and the hydroxyl radical, alkoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, nitro radical, carboxyl radical or alkoxycarbonyl radical, the alkyl part of which contains 1 to 4 carbon atoms, or a phenyl radical, optionally substituted by one or a number of radicals, which are identical or different, chosen from the alkyl radicals containing 1 to 4 carbon atoms or the alkoxy radicals containing 1 to 4 carbon atoms, or a saturated or unsaturated nitrogen-containing heterocyclyl radical containing 5 or 6 members, optionally substituted by one or a number of alkyl radicals containing 1 to 4 carbon atoms, it being understood that the cycloalkyl, cycloalkenyl or bicycloalkyl radicals may optionally be substituted by one or a number of alkyl radicals containing 1 to 4 carbon atoms, and Het represents an aromatic heterocyclic radical having 5 members and containing one or a number of atoms, which are identical or different, chosen from the nitrogen, oxygen or sulphur atoms, such as thiophene, thiazole, furan, pyrrole, imidazole, isoxazole or pyrazole, optionally substituted by one or a number of substituents, which are identical or different, chosen from the halogen atoms (fluorine, chlorine) and the alkyl, containing 1 to 4 carbon atoms, aryl, containing 6 to 10 carbon atoms, alkoxy, containing 1 to 4 carbon atoms, aryloxy, containing 6 to 10 carbon atoms, amino, alkylamino, containing 1 to 4 carbon atoms, dialkylamino, each alkyl part of which contains 1 to 4 carbon atoms, acylamino, the acyl part of which contains 1 to 4 carbon atoms, alkoxycarbonylamino, containing 1 to 4 carbon atoms, acyl, containing 1 to 4 carbon atoms, arylcarbonyl, the aryl part of which contains 6 to 10 carbon atoms, cyano, nitro, hydroxyl, carboxyl, carbamoyl, alkylcarbamoyl, the alkyl part of which contains 1 to 4 carbon atoms, dialkylcarbamoyl, each alkyl part of which contains 1 to 4 carbon atoms, or alkoxycarbonyl, the alkoxy part of which contains 1 to 4 carbon atoms, radicals, with the exception of Het representing a 2-furyl or 2-thienyl radical when $R_1$ represents a benzoyl radical or when $R_2$ represents an alkyl radical containing 1 to 6 carbon atoms.

The products of general formula (I) in which R represents a hydrogen atom or an acetyl radical, $R_1$ represents a benzoyl radical or a radical $R_2$—O—CO— in which $R_2$ represents a t-butyl radical and Het represents a 3-thienyl or 3-furyl radical are very particularly advantageous.

The new products of general formula (I) have biological properties.

In vitro, the measurement of the biological activity is carried out on tubulin extracted from pig brain by the method of M. L. Shelanski et al., Proc. Natl. Acad. Sci. USA, 70, 765–768 (1973). The study of the depolymerization of the microtubules to tubulin is carried out according to the method of G. Chauvière et al., C. R. Acad. Sci. 293, series II, 501–503 (1981). In this study, the products of general formula (I) were shown to be at least as active as taxol and Taxotere.

In vivo, the products of general formula (I) were shown to be active in mice grafted with melanoma B16 at doses between 1 and 10 mg/kg intraperitonealy, as well as on other liquid or solid tumours.

EXAMPLES

The following examples illustrate the present invention.

Example 1

0.077 g of sodium hydrogencarbonate and then dropwise, at a temperature in the region of 20° C., a solution of 0.219 g of di-tert-butyl dicarbonate in 10 cm³ of dichloromethane are added to a solution of 0.67 g of 4-acetoxy-2α-benzoyloxy-5α,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(3-thienyl)propionate in 10 cm³ of dichloromethane, maintained under an argon atmosphere. The solution obtained is stirred for 20 hours at a temperature in the region of 20° C. and then a mixture of 25 cm³ of distilled water and of 20 cm³ of dichloromethane is added. The aqueous phase is separated by settling and then extracted with 20 cm³ of dichloromethane. The organic phases are combined, dried over magnesium sulphate, filtered and then concentrated to dryness under reduced pressure (2.7 kPa) at 40° C. There is obtained 0.76 g of a white foam which is purified by chromatography on 40 g of silica (0.063–0.2 mm) contained in a column with a diameter of 2 cm [eluent: dichloromethane/methanol (99/1 by volume)], 3 cm³ fractions being collected. The fractions containing only the desired product are combined and concentrated to dryness under reduced pressure (2.7 kPa) at a temperature in the region of 40° C. There is thus obtained 0.564 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(3-thienyl)-2-hydroxypropionate in the form of a white foam.

A solution of 0.564 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(3-thienyl)-2-hydroxypropionate in a mixture of 10 cm³ of methanol and of 10 cm³ of acetic acid is heated with stirring and under an argon atmosphere to a temperature in the region of 60° C. and then 1.2 g of zinc powder are added. The reaction mixture is then stirred for 15 minutes at 60° C., then cooled to a temperature in the region of 20° C. and filtered through sintered glass covered with Celite. The sintered glass is washed with 3 times 10 cm³ of dichloromethane and the filtrates are combined and then concentrated to dryness under reduced pressure (2.7 kPa) at a temperature in the region of 40° C.

25 cm³ of distilled water are added to the residue and the crystallized solid is separated by filtration, washed with 4 times 5 cm³ of distilled water and dried under reduced pressure (0.27 kPa) at 20° C. for 16 hours. There is obtained 0.30 g of a white foam which is purified by chromatography on 40 g of silica (0.063–0.2 mm) contained in a column with a diameter of 2 cm [eluent: dichloromethane/methanol (97/3 by volume)], 5 cm³ fractions being collected. The fractions which contain only the desired product are combined and concentrated to dryness under reduced pressure (0.27 kPa) at 40° C. for 16 hours. There is thus obtained 0.18 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(3-thienyl)-2-hydroxypropionate in the form of a white foam, the characteristics of which are the following:

optical rotation: $[\alpha]_D^{20} = -30°$ (c=0.36, methanol)

NMR spectrum: (400 MHz, CDCl₃, δ in ppm): 1.20 (s, 3H, —CH₃ 16 or 17), 1.30 (s, 3H, —CH₃ 16 or 17), 1.40 (s, 9H, —C(CH₃)₃), 1.70 (s, 1H, —OH1), 1.82 (s, 3H, —CH₃ 19), 1.88 (m, 1H, —(CH)—H6), 1.95 (s, 3H, —CH₃ 18), 2.40 (m, 5H, —CH₂—14 and —COCH₃), 2.62 (m, 1H, —(CH)—H6), 3.40 (d, 1H, —OH 2'), 4.00 (d, 1H, —H3), 4.20 (bs, 1H, —OH10), 4.25 (m, 2H, —H7 and —(CH)—H 20), 4.35 (d, 1H, —(CH)—H20), 4.65 (dd, 1H, —H2'), 4.97 (dd, 1H, —H5), 5.20 to 5.40 (m, 3H, —H3', —H10 and —NHCOOC(CH₃)₃), 5.75 (d, 1H, —H2), 6.25 (t, 1H, —H13), 7.15 (d, 1H, 3-thienyl-(—H4)), 7.35 (bs, 1H, 3-thienyl-(—H2)), 7.40 (dd, 1H, 3-thienyl-(—H5)), 7.55 (dd, 2H, —OCOC₆H₅(—H3 and —H5)), 7.65 (t, 1H, —OCOC₆H₅(—H4)), 8.15 (d, 2H, —OCOC₆H₅(—H2 and —H6)).

4-Acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(3-thienyl)propionate can be prepared in the following way:

A solution of 0.87 g of 4-acetoxy-2α-benzoyloxy-5α,20-epoxy-1-hydroxy-9-oxo -7β, 10β-bis[(2,2,2-trichloroethoxy)carbonyloxy]-11-taxen-13α-yl (2RS,4S,5R)-3-tert-butoxycarbonyl-2-(4-methoxyphenyl)-4-(3-thienyl)oxazolidine-5-carboxylate in 8 cm³ of formic acid is stirred for 4 hours at a temperature in the region of 20° C. and then concentrated to dryness under reduced pressure (2.7 kPa) at 40° C. A mixture of 100 cm³ of dichloromethane and of 15 cm³ of a saturated aqueous sodium hydrogencarbonate solution is added to the residue. The aqueous phase is separated by settling and extracted with 15 cm³ of dichloromethane. The organic phases are combined, dried over magnesium sulphate, filtered and then concentrated to dryness under reduced pressure (2.7 kPa) at 40° There is obtained 0.73 g of a white foam which is purified by chromatography on 40 g of silica (0.063–0.2 mm) contained in a column with a diameter of 2 cm [eluent: dichloromethane/methanol (98/2 by volume)], 5 cm³ fractions being collected. The fractions which contain only the desired product are combined and concentrated to dryness under reduced pressure (2.7 kPa) at a temperature in the region of 40° C. There is thus obtained 0.455 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(3-thienyl)propionate in the form of white foam.

4-Acetoxy-2α-benzoyloxy-5β,20-epoxy-1-hydroxy-9-oxo-7β,10β-bis[(2,2,2trichloroethoxy)carbonyloxy]-11-taxen-13α-yl (2RS,4S,5R)-3-tert-butoxycarbonyl-2-(4-methoxyphenyl)-4-(3-thienyl)oxazolidine-5-carboxylate can be prepared in the following way:

A solution of 0.45 g of (2RS,4S,5R)-3-tert-butoxycarbonyl-2-(4-methoxyphenyl)-4-(3-thienyl)oxazolidine-5-carboxylic acid and of 0.602 g of 4-acetoxy-2α-benzoyloxy-5β,20-epoxy-1,13α-dihydroxy-9-oxo-7β,10β-bis[(2,2,2-trichloroethoxy)carbonyloxy]-11-taxene in 100 cm³ of toluene is dehydrated by azeotropic distillation of the toluene at a temperature in the region of 60° C. and under a pressure of 13.3 kPa. 10 cm³ of toluene are thus removed in 20 minutes. After having cooled the reaction mixture to a temperature in the region of 20° C., 0.277 g of N,N'-dicyclohexylcarbodiimide and 0.041 g of 4-dimethylaminopyridine are added. The reaction medium is then stirred for 1 hour 30 minutes at a temperature in the region of 20° C. and then a mixture of 250 cm³ of dichloromethane and of 7 cm³ of a saturated aqueous sodium hydrogencarbonate solution is added. The aqueous phase is separated by settling and then extracted with 15 cm³ of dichloromethane. The organic phases are combined, dried over magnesium sulphate, filtered and then concentrated to dryness under reduced pressure (2.7 kPa) at 50° C. There are obtained 1.36 g of a white foam which is purified by chromatography on 50 g of silica (0.063–0.2 mm) contained in a column with a diameter of 2 cm [eluent: dichloromethane/methanol (99/1 by volume)], 10 cm³ fractions being collected. The fractions containing only the desired product are combined and concentrated to dryness under reduced pressure (2.7 kPa) at a temperature in the region of 40° C. There is thus obtained 0.83 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2RS,4S,5R)-3-tert-butoxycarbonyl-2-(4-methoxyphenyl)-4-(3-thienyl)oxazolidine-5-carboxylate in the form of white foam.

4-Acetoxy-2α-benzoyloxy-5β,20-epoxy-1,13α-dihydroxy-9-oxo-7β,10β-bis[(2,2,2-trichloroethoxy)carbonyloxy]-11-taxene can be prepared according to the method described in European Patent EP-0,336,841.

(2RS,4S,5R)-3-tert-Butoxycarbonyl-2-(4-methoxyphenyl)-4-(3-thienyl)oxazolidine-5-carboxylic acid can be prepared in the following way:

A solution of 0.4 g of lithium hydroxide hydrate in 1.5 cm³ of distilled water is added, at a temperature in the region of 25° C., to a solution of 1.36 g of ethyl (2RS,4S,5R)-3-tert-butoxycarbonyl-2-(4-methoxyphenyl)-4-(3-thienyl)oxazolidine-5-carboxylate in 20 cm³ of ethanol. The reaction medium is stirred for 1 hour at a temperature in the region of 25° C. and then concentrated to dryness under reduced pressure (2.7 kPa) at a temperature in the region of 40° C. The residue obtained is dissolved in 50 cm³ of distilled water and then extracted with 3 times 50 cm³ of diethyl ether. The aqueous phase is then acidified to a pH in the region of 1 with a 1N aqueous hydrochloric acid solution and then extracted with 3 times 50 cm³ of dichloromethane.

The organic phases are combined, dried over magnesium sulphate, filtered and then concentrated to dryness under reduced pressure (2.7 kPa) at a temperature in the region of 40° C. There is thus obtained i g of (2RS,4S,5R)-3-tert-butoxycarbonyl-2-(4-methoxyphenyl)-4-(3-thienyl)oxazolidine-5-carboxylic acid in the form of a white foam.

Ethyl (2RS,4S,5R)-3-tert-butoxycarbonyl-2-(4-methoxyphenyl)-4-(3-thienyl)oxazolidine-5-carboxylate can be prepared in the following way:

A solution of 1.9 g of ethyl (2R,3S)-3-tert-butoxycarbonylamino-2-hydroxy-3-(3-thienyl)propionate and of 75 mg of pyridinium p-toluenesulphonate in 18 cm³ of toluene is heated to boiling and the distillate is collected in a Dean and Stark apparatus. After having removed 10 cm³ of distillate, a solution of 1.06 cm³ of the dimethyl acetal of anisaldehyde in 6 cm³ of toluene is added dropwise and reflux is maintained for 2 hours 30 minutes. The reaction medium is cooled to a temperature in the region of 40° C. and concentrated to dryness under reduced pressure (2.7 kPa) at a temperature in the region of 40° C. There are obtained 2.62 g of a brown oil which is purified by chromatography on 100 g of silica (0.04–0.063 mm) contained in a column with a diameter of 5 cm [eluent: petroleum ether/diethyl ether (80/20 by volume)], 4 cm³ fractions being collected. The fractions containing only the desired product are combined and concentrated to dryness under reduced pressure (2.7 kPa) at a temperature in the region of 40° C. There are thus obtained 1.8 g of ethyl (2RS,4S,5R)-3-tert-butoxycarbonyl-2-(4-methoxyphenyl)-4-(3-thienyl)oxazolidine-5-carboxylate in the form of a yellow oil.

Ethyl (2R,3S)-3-tert-butoxycarbonylamino-2-hydroxy-3-(3-thienyl)propionate can be prepared in the following way:

1.65 g of sodium hydrogencarbonate and then dropwise, at a temperature in the region of 20° C., a solution of 4.7 g of di-tert-butyl dicarbonate in 10 cm³ of dichloromethane are added to a solution of 3.75g of ethyl (2R,3S)-3-amino-2-hydroxy-3-(3-thienyl)propionate in 100 cm³ of dichloromethane, maintained under an argon atmosphere. The solution obtained is stirred for 72 hours at a temperature in the region of 20° C. and then 60 cm³ of distilled water are added. The aqueous phase is separated by settling and then extracted with 3 times 50 cm³ of dichloromethane. The organic phases are combined, dried over magnesium sulphate, filtered and then concentrated to dryness under reduced pressure (2.7 kPa) at 40° C. There are obtained 9.15 g of a brown oil which is purified by chromatography on 300 g of silica (0.063–0.2 mm) contained in a column with a diameter of 5 cm [eluent: cyclohexane/ethyl acetate (70/30 by volume)], 20 cm³ fractions being collected. The fractions containing only the desired product are combined and concentrated to dryness under reduced pressure (2.7 kPa) at a temperature in the region of 40° C. There are thus obtained 4.95 g of ethyl (2R,3S)-3-tert-butoxycarbonylamino-2-hydroxy-3-(3-thienyl)propionate in the form of a colorless oil which crystallizes at room temperature.

Ethyl (2R,3S)-3-amino-2-hydroxy-3-(3-thienyl)propionate can be prepared in the following way:

0.2 g of 10% palladium-on-charcoal powder is added to a solution of 4.3 g of ethyl (2R,3S)-3-azido-2-hydroxy-3-(3-thienyl)propionate in 70 cm³ of ethyl acetate. The reaction mixture is stirred under a pressure of 120 kPa of hydrogen and at a temperature in the region of 22° C. for 21 hours and then filtered through sintered glass covered with Celite. The sintered glass is washed with 3 times 5 cm³ of ethyl acetate and the filtrates are combined and then concentrated to dryness under reduced pressure (2.7 kPa) at a temperature in the region of 40° C. There are thus obtained 3.75 g of ethyl (2R,3S)-3-amino-2-hydroxy-3-(3 thienyl)propionate in the form of white crystals melting at 85° C.

Ethyl (2R,3S)-3-azido-2-hydroxy-3-(3-thienyl)propionate can be prepared in the following way:

9.6 cm³ of a 1.6M solution of n-butyllithium in hexane and then, dropwise, a solution of 3.1 g of (4S,SR)-(2S,3R)-3-[2-bromo-3-hydroxy-3-(3-thienyl)-1-oxopropyl]-4-methyl-5-phenyloxazolidin-2-one in 50 cm³ of tetrahydrofuran are added, while maintaining the temperature at −75° C., to a solution, cooled to a temperature in the region of −75° C., of 0.9 cm³ of ethanol in 15 cm³ of anhydrous tetrahydrofuran. The reaction medium is reheated to a temperature in the region of 15° C., then maintained at 15° C. for 15 minutes and recooled again to a temperature in the region of −75° C. A solution of 2.0 g of citric acid in 10 cm³ of tetrahydrofuran is then added while maintaining the temperature at −75° C. The reaction medium is reheated to a temperature in the region of −10° C. and 20 cm³ of distilled water are added. The organic phase is separated by settling and washed with 2 times 10 cm³ of a saturated sodium chloride solution.

25 cm³ of ethylene glycol monomethyl ether, 25 cm³ of distilled water, 2.45 g of sodium azide and 1.0 g of ammonium chloride are successively added to this organic phase. The reaction mixture is stirred at reflux for 30 hours and then cooled to a temperature in the region of 20° C. The organic solvents are removed by concentrating under reduced pressure (2.7 kPa) at 40° C.

10 cm³ of diethyl ether are added to the residue obtained. The aqueous phase is separated by settling and extracted with 4 times 10 cm³ of diethyl ether. The organic phases are combined, dried over magnesium sulphate, filtered and then concentrated to dryness under reduced pressure (2.7 kPa) at 40° C. There are obtained 2.47 g of an orange oil which is purified by chromatography on 100 g of silica (0.063–0.2 mm) contained in a column with a diamter of 2 cm [eluent: cyclohexane/ethyl acetate (90/10 by volume)], 5 cm³ fractions being collected. The fractions containing only the desired product are combined and concentrated to dryness under reduced pressure (2.7 kPa) at a temperature in the region of 40° C. There are thus obtained 1.44 g of ethyl (2R,3S)-3-azido-2-hydroxy-3-(3-thienyl)propionate in the form of a pale-yellow oil.

(4S,5R)-(2S,3R)-3-[2-Bromo-3-hydroxy-3-(3-thienyl)-1-oxopropyl]-4-methyl-5-phenyloxazolidin-2-one can be prepared in the following way:

12.6 cm³ of triethylamine and then, dropwise, 70.4 cm³ of a 1M solution of di-n-butylboron triflate in dichloromethane are added, at a temperature in the region of 20° C., to a solution of 19 g of (4S,5R)-3-(2-bromo-1-oxoethyl)-4-methyl-5-phenyloxazolidin-2-one in 300 cm³ of anhydrous diethyl ether. The reaction medium is cooled to a temperature in the region of −75° C., a solution of 4.2 cm³ of thiophene-3-carbaldehyde in 10 cm³ of diethyl ether is then added while maintaining the temperature at −75° C., and the reaction medium is reheated to a temperature in the region of 0° C. and maintained at 0° C. for 1 hour 30 minutes. 40 cm³ of a saturated sodium hydrogensulphate solution are then added, the aqueous phase is separated by settling and extracted with 2 times 50 cm³ of diethyl ether. The organic phases are combined, dried over magnesium sulphate, filtered and then concentrated to dryness under reduced pressure (2.7 kPa) at 40° There are obtained 43.2 g of a brown oil which is purified by chromatography on 500 g of silica (0.063–0.2 mm) contained in a column with a diameter of 5 cm [eluent: cyclohexane/ethyl acetate (90/10 by volume)], 100 cm³ fractions being collected. The fractions containing only the desired product are combined and concentrated to dryness under reduced pressure (2.7 kPa) at a temperature in the region of 40° C. There are thus obtained, after crystallization from diisopropyl ether, 14 g of (4S,5R)-(2S,3R)-3-[2-bromo-3-hydroxy-3-(3-thienyl)-1-oxopropyl]-4-methyl-5-phenyloxazolidin-2-one melting at 124° C.

(4S,5R)-3-(2-Bromo-1-oxoethyl)-4-methyl-5-phenyloxazolidin-2-one can be prepared under the conditions described in International Application PCT WO 92/09589.

Example 2

0.066 g of sodium hydrogencarbonate and then, dropwise, at a temperature in the region of 20° C., a solution of 0.188 g of di-tert-butyl dicarbonate in 10 cm³ of dichloromethane are added to a solution of 0.75 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(3-furyl)propionate in 40 cm³ of dichloromethane, maintained under an argon atmosphere. The solution obtained is stirred for 20 hours at a temperature in the region of 20° C. and then a mixture of 25 cm³ of distilled water and of 20 cm³ of dichloromethane is added. The aqueous phase is separated by settling and then extracted with 20 cm³ of dichloromethane. The organic phases are combined, dried over magnesium sulphate, filtered and then concentrated to dryness under reduced pressure (2.7 kPa) at 40° C. There is obtained 0.85 g of a white foam which is purified by chromatography on 70 g of silica (0.063–0.2 mm) contained in a column with a diameter of 2.5 cm [eluent: dichloromethane/methanol (99/1 by volume)], 5 cm³ fractions being collected. The fractions containing only the desired product are combined and concentrated to dryness under reduced pressure (2.7 kPa) at a temperature in the region of 40° C. There is thus obtained 0.74 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(3-furyl)-2-hydroxypropionate in the form of a white foam.

A solution of 0.73 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(3-furyl)-2-hydroxypropionate in a mixture of 15 cm³ of methanol and of 15 cm³ of acetic acid is heated with stirring and under an argon atmosphere to a temperature in the region of 60° C. and then 1.5 g of zinc powder are added. The reaction mixture is then stirred for 10 minutes at 60° C., then cooled to a temperature in the region of 20° C. and filtered through sintered glass covered with Celite. The sintered glass is washed with 3 times 10 cm³ of methanol and the filtrates are combined and then concentrated to dryness under reduced pressure (2.7 kPa) at a temperature in the region of 40° C.

15 cm³ of distilled water are added to the residue and the crystallized solid is separated by filtration, washed with 6 times 5 cm³ of distilled water and dried under reduced pressure (0.27 kPa) at 20° C. for 16 hours. There is obtained 0.49 g of a white foam which is purified by chromatography on 40 g of silica (0.063–0.2 mm) contained in a column with a diameter of 2 cm [eluent: dichloromethane/methanol (97/3 by volume)], 5 cm³ fractions being collected. The fractions containing only the desired product are combined and concentrated to dryness under reduced pressure (0.27 kPa) at 40° C. for 16 hours. There is thus obtained 0.31 g of 4-acetoxy-2α-benzoyloxy-5β,20-epoxy-1,7β,10β-trihydroxy-9-oxo-11-taxen-13α-yl (2R,3S)-3-tert-butoxycarbonylemino -3-(3-furyl)-2-hydroxypropionate in the form of a white foam, the characteristics of which are the following:

optical rotation: $[\alpha]_D^{20} = -33°$ (c=0.47, methanol)

NMR spectrum: (400 MHz, CDCl$_3$, δ in ppm): 1.20 (s, 3H, —C$\underline{H}_3$ 16 or 17), 1.30 (s, 3H, —C$\underline{H}_3$ 16 or 17), 1.40 (s, 9H, —C(C$\underline{H}_3$)$_3$), 1.72 (s, 1H, —O$\underline{H}$1), 1.80 (s, 3H, —CH$_3$ 19), 1.90 (m, 1H, —(CH)—$\underline{H}$6), 1.92 (s, 3H, —CH$_3$ 18), 2.35 (m, 5H, —C$\underline{H}_2$—14 and —COC$\underline{H}_3$), 2.60 (m, 1H, —(CH)—$\underline{H}$6), 3.50 (d, 1H, —O$\underline{H}$2'), 3.95 (d, 1H, —$\underline{H}$3), 4.25 (m, 3H, —O$\underline{H}$10, —(CH)—H 20 and —$\underline{H}$7), 4.35 (d, 1H, —(CH)—$\underline{H}$20), 4.58 (dd, 1H, —$\underline{H}$2'), 5.00 (dd, 1H, —$\underline{H}$5), 5.20 (m, 3H, —$\underline{H}$3', —$\underline{H}$10 and —N$\underline{H}$-COOC(CH$_3$)$_3$), 5.70 (d, 1H, —$\underline{H}$2), 6.25 (t, 1H, —$\underline{H}$3), 6.50 (bs, 1H, 3-furyl-(—$\underline{H}$7.45 (bd, 1H, 3-furyl-(—$\underline{H}$2)), 7.55 (m, 3H, —OCOC$_6$H$_5$(—$\underline{H}$3 and —$\underline{H}$5) and 3-furyl-(—$\underline{H}$5)), 7.65 (t, 1H, —OCOC$_6$H$_5$ (—$\underline{H}$4)), 8.15 (d, 2H, —OCOC$_6$H$_5$(—$\underline{H}$2 and —$\underline{H}$6)).

4-Acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(3-furyl) propionate can be prepared in the following way:

A solution of 1.15 g of 4-acetoxy-2α-benzoyloxy -5β,20-epoxy -1-hydroxy -9-oxo -7β,10β-bis[(2,2,2-trichloroethoxy)carbonyloxy]-11-taxen-13α-yl (2RS,4S,5R)-3-tert-butoxycarbonyl -2-(4-methoxyphenyl)-4-(3-furyl)oxazolidine-5-carboxylate in 20 cm³ of formic acid is stirred for 4 hours at a temperature in the region of 20° C. and then concentrated to dryness under reduced pressure (2.7 kPa) at 40° C. A mixture of 100 cm³ of dichloromethane and of 25 cm³ of a saturated aqueous sodium hydrogencarbonate solution is added to the residue. The aqueous phase is separated by settling and extracted with 15 cm³ of dichloromethane. The organic phases are combined, dried over magnesium sulphate, filtered and then concentrated to dryness under reduced pressure (2.7 kPa) at 40° C. There are obtained 1.5 g of a white foam which is purified by chromatography on 70 g of silica (0.063–0.2 mm) contained in a column with a diameter of 2.5 cm eluent: dichloromethane/methanol (98/2 by volume), 5 cm³ fractions being collected. The fractions containing only the desired product are combined and concentrated to dryness under reduced pressure (2.7 kPa) at a temperature in the region of 40° C. There is thus obtained 0.76 g of 4-acetoxy-2α-benzoyloxy-5β,20-epoxy-1-hydroxy-9-oxo-7β,10β-bis[(2,2,2-trichloroethoxy) carbonyloxy]-11-taxen-13α-yl (2R,3S)-3-amino-2-hydroxy-3-(3-furyl)propionate in the form of an orangey foam.

4-Acetoxy-2α-benzoyloxy-5β,20-epoxyl-1-hydroxy-9-oxo-7β,10β-bis[(2,2,2-trichloroethoxy)carbonyloxy]-11-taxen-13α-yl (2RS,4S,5R)-3-tert-butoxycarbonyl-2-(4-methoxyphenyl)-4-(3-furyl)oxazolidine-5-carboxylate can be prepared in the following way:

A solution of 0.66 g of (2RS,4S,5R)-3-tert-butoxycarbonyl-2-(4-methoxyphenyl)-4-(3-furyl)oxazolidine-5-carboxylic acid and of 1.0 g of 4-acetoxy-2α-benzoyloxy-5β,20-epoxy-1,13α-dihydroxy-9-oxo-7β,10β-bis[(2,2,2-trichloroethoxy)carbonyloxy]-11-taxene in 50 cm³ of toluene is dehydrated by azeotropic distillation of the toluene at a temperature in the region of 60° C. and under a pressure of 13.3 kPa. 10 cm³ of toluene are thus removed in 20 minutes. After having cooled the reaction medium to a temperature in the region of 20° C., 0.450 g of N,N'-dicyclohexylcarbodiimide and 0.067 g of 4-dimethylaminopyridine are added. The reaction medium is then stirred for 2 hours 30 minutes at a temperature in the region of 20° C. and then a mixture of 250 cm³ of dichloromethane and of 25 cm³ of a saturated aqueous sodium hydrogencarbonate solution are then added. The aqueous phase is separated by settling and then extracted with 50 cm³ of dichloromethane. The organic phases are combined, dried over magnesium sulphate, filtered and then concentrated to dryness under reduced pressure (2.7 kPa) at 40° C. There are obtained 3.0 g of a white foam which is purified by chromatography on 80 g of silica (0.063–0.2 mm) contained in a column with a diameter of 2.5 cm [eluent: dichloromethane/methanol (99.5/0.5 by volume)], 10 cm³ fractions being collected. The fractions containing only the desired product are combined and concentrated to dryness under reduced pressure (2.7 kPa) at a temperature in the region of 40° C. There are thus obtained 1.15 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2RS,4S,5R)-3-tert-butoxycarbonyl-2-(4-methoxyphenyl)-4-(3-furyl)oxazolidine-5-carboxylate in the form of a white foam.

(2RS,4S,5R)-3-tert-Butoxycarbonyl-2-(4-methoxyphenyl)-4-(3-furyl)oxazolidine-5-carboxYlic acid can be prepared in the following way:

A solution of 0.24 g of lithium hydroxide hydrate in 7 cm³ of distilled water is added, at a temperature in the region of 25° C., to a solution of 0.775 g of methyl (2RS,4S,5R)-3-tert-butoxycarbonyl-2-(4-methoxyphenyl)-4-(3-furyl)oxazolidine-5-carboxylate in 20 cm³ of ethanol.

The reaction medium is stirred for 15 minutes at a temperature in the region of 25° C. and then concentrated to dryness under reduced pressure (2.7 pKa) at a temperature in the region of 40° C. The residue obtained is dissolved in 30 cm³ of distilled water and then extracted with 3 times 50 cm³ of diethyl ether. The aqueous phase is then acidified to a pH in the region of 3 with a 2N aqueous hydrochloric acid solution and then extracted with 3 times 25 cm³ of dichloromethane. The organic phases are combined, dried over magnesium sulphate, filtered and then concentrated to dryness under reduced pressure (2.7 kPa) at a temperature in the region of 40° C. There is thus obtained 0.690 g of (2RS,4S,5R)-3-tert-butoxycarbonyl-2-(4-methoxyphenyl)-4-(3-furyl)oxazolidine-5-carboxylic acid in the form of a white foam.

Methyl (2RS,4S,5R)-3-tert-butoxycarbonyl-2-(4-methoxyphenyl )-4-(3-furyl)oxazolidine-5-carboxylate can be prepared in the following way:

A solution of 0.75 g of methyl (2R,3S)-3-tert-butoxycarbonylamino-2-hydroxy-3-(3-furyl)propionate and of 33 mg of pyridinium p-toluenesulphonate in 35 cm³ of toluene is heated to boiling and the distillate is collected in a Dean and Stark apparatus. After having removed 10 cm³ of distillate, a solution of 0.446 cm³ of the dimethyl acetal of anisaldehyde in 5 cm³ of toluene is added dropwise and reflux is maintained for 1 hour 30 minutes. The reaction medium is cooled to a temperature in the region of 40° C. and concentrated to dryness under reduced pressure (2.7 kPa) at a temperature in the region of 40° C. There are obtained 1.4 g of a brown oil which is purified by chromatography on 70 g of silica (0.063–0.2 mm) contained in a column with a diameter of 2.5 cm [eluent: dichloromethane/methanol (99.5/0.5 by volume)], 5 cm³ fractions being collected. The fractions containing only the desired product are combined and concentrated to dryness under reduced pressure (2.7 kPa) at a temperature in the region of 40° C. There is thus obtained 0.8 g of methyl (2RS,4S,5R)-3-tert-butoxycarbonyl-2-(4-methoxyphenyl)-4-(3-furyl)oxazolidine-5-carboxylate in the form of a pale-yellow oil.

Methyl (2R,3S)-3-tert-butoxycarbonylamino-2-hydroxy-3-(3-furyl)propionate can be prepared in the following way:

0.46 g of sodium hydrogencarbonate and then, dropwise, at a temperature in the region of 20° C., a solution of 1.23 g of di-tert-butyl dicarbonate in 5 cm³ of dichloromethane are added to a solution of 0.92 g of methyl (2R,3S)-3-amino-2-hydroxy-3-(3-furyl)propionate in 30 cm³ of dichloromethane, maintained under an argon atmosphere. The solution obtained is stirred for 20 hours at a temperature in the region of 20° C. and then 30 cm³ of distilled water are added. The aqueous phase is separated by settling and then extracted with 3 times 25 cm³ of dichloromethane. The organic phases are combined, dried over magnesium sulphate, filtered and then concentrated to dryness under reduced pressure (2.7 kPa) at 40° C. There are obtained 1.36 g of a pale-yellow oil which crystallizes at room temperature.

Methyl (2R,3S)-3-amino-2-hydroxy-3-furyl propionate can be prepared in the following way:

A solution of 2.42 g of methyl (2R,3S)-2-hydroxy-3-[(S)-1-phenyl]ethylamino]-3-furyl propionate in a mixture of 40 cm³ of methanol and 0.48 cm³ of acetic acid is added to 3.0 g of a 3% dispersion of palladium in powdered activated charcoal. The reaction mixture is stirred for 1 hour at 20° C. under a pressure of 120 kPa of hydrogen. The reaction mixture is then filtered through sintered glass covered with Celite. The sintered glass is washed with 3 times 15 cm³ of methanol and the filtrates are combined and then concentrated to dryness under reduced pressure (2.7 kPa) at a temperature in the region of 40° C. 40 cm³ of distilled water are added to the residue and the mixture is basified to a pH in the region of 7 by addition of a 7.5N aqueous sodium hydroxide solution and then extracted with 4 times 100 cm³ of dichloromethane. The organic phases are combined, dried over magnesium sulphate, filtered and then concentrated to dryness under reduced pressure (2.7 kPa) at 40° C. The brown residual oil is purified by chromatography on 60 g of silica (0.04–0.063 mm) contained in a column with a diameter of 2.5 cm [eluent: ethyl acetate/methanol (99/5 by volume)]. The fractions containing only the desired product are combined and concentrated to dryness under reduced pressure (2.7 kPa) at a temperature in the region of 40° C. There is thus obtained 0.93 g of methyl (2R,3S)-3-amino-2-hydroxy-3-furyl propionate in the form of a yellow oil.

Methyl (2R,3S)-2-hydroxy-3-[((S)-1-phenyl]ethylamino-3-furyl propionate can be prepared in the following way:

A solution of 2.18 g of (3R,4S)-3-hydroxy-4-(3-furyl)-1-[(S)-1-phenyl]ethyl-2-azetidinone in a mixture of 40 cm³ of methanol and of 4 cm³ of a 12N aqueous hydrochloric acid solution is heated at reflux (65° C.) for 16 hours, then cooled to a temperature in the region of 20° C. and concentrated to dryness under reduced pressure (2.7 kPa) at a temperature in the region of 40° C. 50 cm³ of distilled water are added to the residue and the mixture is basified to a pH in the region of 7 by addition of a 7.5N aqueous sodium hydroxide solution and then extracted with 3 times 50 cm³ of ethyl acetate. The organic phases are combined, dried over magnesium sulphate, filtered and then concentrated to dryness under reduced pressure (2.7 kPa) at 40° C. There are thus obtained 2.48 g of methyl (2R,3S)-2-hydroxy-3-[((S)-1-phenyl]ethylamino-3-furyl propionate in the form of a pale-yellow oil.

(3R,4S)-3-Hydroxy-4-(3-furyl)-1-[(S)-1-phenyl]ethyl-2-azetidinone can be prepared in the following way:

A solution of 9.24 g of a mixture, in a 70/30 molar proportion, of the two diastereoisomers of 3-acetoxy-4-(3-furyl)-1-[(S)-1-phenyl]ethyl-2-azetidinone, form A and form B, in 200 cm³ of tetrahydrofuran is added over 35 minutes, with stirring and at a temperature in the region of 0° C., to a mixture of 213 cm³ of a 1N aqueous potassium hydroxide solution and of 200 cm³ of tetrahydrofuran.

On completion of the addition, the reaction medium is stirred at a temperature in the region of 0° C. for 1 hour and then 200 cm³ of a saturated aqueous sodium hydrogencarbonate solution and 200 cm³ of distilled water are added. The aqueous phase is separated by settling and extracted with 3 times 200 cm³ of ethyl acetate. The organic phases are combined, dried over magnesium sulphate, filtered and then concentrated to dryness under reduced pressure (2.7 kPa) at 40° C. There are thus obtained 8.1 g of a yellow oil which is crystallized from 100 cm³ of a mixture of ethyl acetate and hexane (60/40 by volume) to give 3.53 g of (3R,4S)-3-hydroxy-4-(3-furyl)-1-[(S)-1-phenyl]ethyl-2-azetidinone in the form of white crystals melting at 100° C.

The mixture, in a 70/30 molar proportion, of the two diastereoisomers of 3-acetoxy-4-(3-furyl)-1-[(S)-1-phenyl]ethyl-2-azetidinone, form A and form B, can be prepared in the following way:

15.5 cm³ of triethylamine are added, with stirring and at a temperature in the region of −15° C., and 5.0 cm³ of 2-acetoxyacetyl chloride are added dropwise, over 75 minutes and while being maintained at this temperature, to a solution of 11.69 g of (S)-1-phenyl-N-[3-furylidene]ethylamine in 100 cm³ of toluene. The solution obtained is reheated to a temperature in the region of 20° C. and maintained at this temperature, with stirring, for 16 hours and then 300 cm³ of a 2.7N aqueous hydrochloric acid solution are added. The organic phase is separated by settling, washed with 2 times 150 cm³ of distilled water and then with 150 cm³ of a saturated aqueous sodium hydrogencarbonate solution, dried over magnesium sulphate, filtered and then concentrated to dryness under reduced pressure (2.7 kPa) at 40° C. There are thus obtained 12.8 g of a brown oil which is purified by chromatography on 400 g of silica (0.04–0.063 mm) contained in a column with a diameter of 5 cm [eluent: cyclohexane/ethyl acetate (80/20 by volume)]. The fractions containing only the desired product are combined and concentrated to dryness under reduced pressure (0.27 kPa) at 40° C. There are thus obtained 0.7 g of a mixture, in a 70/30 molar proportion, of the two diastereoisomers of 3-acetoxy-4-(3-furyl)-1-[(S)-1-phenyl]ethyl-2-azetidinone, form A and form B, in the form of a yellow oil.

(S)-1-Phenyl-N-[3-furylidene]ethylamine can be prepared in the following way:

25.4 cm³ of (S)-1-phenylethylamine and 5 g of 4 Å molecular sieve are added, with stirring and at a temperature in the region of −15° C., to a solution of 19.22 g of furan-3-carbaldehyde in 165 cm³ of dichloromethane. The reaction mixture is reheated to a temperature in the region of 20° C. and maintained at this temperature, with stirring, for 24 hours and then filtered through sintered glass covered with Celite. The sintered glass is washed with 3 times 30 cm³ of dichloromethane and the filtrates are combined and then concentrated to dryness under reduced pressure (2.7 kPa) at a temperature in the region of 40° C. There are thus obtained 39.85 g of (S)-1-phenyl-N-[3-furylidene]ethylamine in the form of a brown oil.

Example 3

A solution of 0.60 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-2-hydroxy-3-(4-thiazolyl)propionate in a mixture of 8 cm³ of methanol and of 8 cm³ of acetic acid is heated with stirring and under an argon atmosphere to a temperature in the region of 60° C. and then 1.2 g of zinc powder are added. The reaction mixture is then stirred for 15 minutes at 60° C., then cooled to a temperature in the region of 20° C. and filtered through sintered glass covered with Celite. The sintered glass is washed with 3 times 10 cm³ of methanol and the filtrates are combined and then concentrated to dryness under reduced pressure (2.7 kPa) at a temperature in the region of 40° C.

10 cm³ of distilled water are added to the residue and the crystallized solid is separated by filtration, washed with 4 times 5 cm³ of distilled water and dried under reduced pressure (0.27 kPa) at 20° C. for 16 hours. There is obtained 0.35 g of a white foam which is purified by chromatography on silica gel deposited on a plate (gel thickness of 0.25 mm. 20×20 cm plates) in 10 mg fractions. After using U.V. radiation to locate the region corresponding to the desired adsorbed product, this region is scraped off and the silica collected is washed on sintered glass with 10 times 10 cm³ of dichloromethane and with 5 times 5 cm³ of methanol. The filtrates are combined and concentrated to dryness under reduced pressure (0.27 kPa) at 40° C. for 16 hours. There is thus obtained 0.135 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-thiazolyl)-2-hydroxypropionate in the form of a white foam, the characteristics of which are the following:

optical rotation: $[ ]_D^{20} = -32 (c=0.57 \text{ methanol})$

N.M.R spectrum: (400 MHz, CDCl$_3$, δ in ppm) 1.12 (s, 3H, —C$\underline{H}_3$ 16 or 17), 1.24 (s, 3H, —C$\underline{H}_3$ 16 or 17), 1.40 (s, 9H, —C(C$\underline{H}_3$)$_3$), 1.70 (s, 1H, —O$\underline{H}$1), 1.78 (s, 3H, —CH$_3$ 19), 1.87 (mt, 1H, —(CH)—$\underline{H}$6), 1.90 (s, 3H, —C$\underline{H}_3$ 18), 2.30 (split ab, J=16 and 9 Hz, 2H, —C$\underline{H}_2$14), 2.45 (s, 3H, —COC$\underline{H}_3$), 2.60 (m,t 1H, —(CH)—$\underline{H}$6), 3.94 (d, J=7 Hz, 1H, $\underline{H}$3), 4.20 (d, J=8 Hz, 1H, —(CH)—$\underline{H}$20), 4.20 (broad, 1H, —O$\underline{H}$10), 4.25 (broad dd, J=11.5 and 7.5 Hz, 1H, —$\underline{H}$7), 4.34 (d, J=8 Hz, 1H, —(CH)—$\underline{H}$20), 4.88 (broad s, 1H, —$\underline{H}$2'), 4.97 (broad d, J=10 Hz, 1H, $\underline{H}$5), 5.20 (s, 1H, —$\underline{H}$10), 5.47 (broad d, J=10 Hz, 1H, $\underline{H}$3'), 5.68 (d, J=10 Hz, 1H, —CON$\underline{H}$), 5.70 (d, J=7 Hz, 1H, —$\underline{H}$2), 6,20 (t, J=9 Hz, 1H, —$\underline{H}$13), 7.32 (broad s, 1H, 4-thiazolyl-(—$\underline{H}$5)), 7.50 (t, J=7.5 Hz, 2H, —OCOC$_6$H$_5$ (—$\underline{H}$3 and —$\underline{H}$5)), 7.60 (t, J=7.5 Hz, 1H, —OCOC$_6$H$_5$(—$\underline{H}$4)), 8.11 (d, J=7.5 Hz, 2H, —OCOC$_6$H$_5$(—$\underline{H}$2 and —$\underline{H}$6)), 8.80 (d, J=1.5 Hz, 1H, 4-thiazolyl-(—$\underline{H}$2)).

By carrying out the reaction as in Example 2, but from suitable starting materials, the following intermediates are prepared:

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-2-hydroxy-3-(4-thiazolyl)propionate in the form of a white foam.

4-acetoxy, 2a-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(4 thiazolyl) propionate in the form of a white foam.

4-acetoxy, 2α-benzoyloxy-5β,20-epoxy-1-hydroxy-9-oxo-7β,10β-bis[(2,2,2-trichloroethoxy)carbonyloxy]-11-taxen-13α-yl (2RS,4S,5R)-3-tert-butoxycarbonyl-2-(4-methoxyphenyl)-4-(4-thiazolyl)oxazolidine -5-carboxylate in the form of a white foam.

(2RS,4S,5R)-3-tert-butoxycarbonyl-2-(4-methoxyphenyl)-4-(4-thiazolyl )oxazolidine -5-carboxylic acid in the form of a white foam.

methyl (2RS,4S,5R)-3-tert-butoxycarbonyl-2-(4-methoxyphenyl)-4-(4-thiazolyl)oxazolidine -5-carboxylate in the form of a pale-yellow oil.

methyl (2R,3S)-3-tert-butoxycarbonylamino-2-hydroxy-3-(4-thiazolyl)propionate in the form of a white foam.

methyl (2R,3S)-3-amino-2-hydroxy-3-(4-thiazolyl)propionate in the form of a pale-yellow oil.

Methyl (2R,3S)-2-hydroxy-3-[((S)-1-phenyl]ethylamino-4-thiazolyl propionate in the form of a pale-yellow oil.

(3R,4S)-3-hydroxy-4-(4-thiazolyl)-1-[(S)-1phenyl]ethyl-2-azetidinone in the form of a white foam.

the mixture, in the molar proportion: 70/30, of the two diastereoisomers of 3-acetoxy-4-(4-thiazolyl)-1-[(S)-1-phenyl]ethyl-1–2-azetidinone, form A and form B, in the form of a pale-yellow oil.

(S)-1-phenyl-N-[4-thiazolylidene]ethylamine in the form of a yellow oil.

thiazole-4-carbaldehyde can be prepared according to the method described by A. Dondoni et al., Synthesis, 1987, 998–1001.

(S)-1-(4-methoxyphenyl)ethylamine can be prepared according to the method described by H.O. Bernhard et al., Helv. Chim. Acta, 1973, 56(4), 1266–1303.

The new products of general formula (I) manifest significant inhibitory activity with respect to abnormal cell proliferation, and possess therapeutic properties that enable patients having pathological conditions associated with an abnormal cell proliferation to be treated. The pathological conditions include the abnormal cell proliferation of malignant or nonmalignant cells of various tissues and/or organs comprising, without implied limitation, muscle, bone or connective tissue, the skin, brain, lungs, sex organs, lymphatic or renal systems, mammary or blood cells, liver, digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanomas, multiple myelomas, chronic lymphocytic leukaemias, and acute or chronic granulocytic lymphomas. The new products according to the invention are especially useful for the treatment of cancer of the ovary. The products according to the invention may be used to prevent or delay the appearance or reappearance of the pathological conditions, or for treating these pathological conditions.

The products according to the invention may be administered to a patient according to different forms suited to the chosen administration route, which is preferably the parenteral route. Parenteral administration comprises intravenous, intraperitoneal, intramuscular or subcutaneous administrations. Intraperitoneal or intravenous administration is more especially preferred.

The present invention also comprises pharmaceutical compositions containing at least one product of general formula (I) in a sufficient amount suitable for use in human or veterinary therapy. The compositions may be prepared according to the customary methods, using one or more pharmaceutically acceptable adjuvants, vehicles or excipients. Appropriate vehicles include diluents, sterile aqueous media and various nontoxic solvents. Preferably, the compositions take the form of aqueous suspensions or solutions, injectable solutions which can contain emulsifying agents, colorants, preservatives or stabilizers.

The choice of adjuvants or excipients may be determined by the solubility and chemical properties of the product, the particular mode of administration and good pharmaceutical practices.

For parenteral administration, sterile aqueous or nonaqueous suspensions or solutions are used. For the preparation of nonaqueous suspensions or solutions, natural vegetable oils such as olive oil, sesame oil or liquid paraffin, or injectable organic esters such as ethyl oleate, may be used. The sterile aqueous solutions can consist of a solution of a pharmaceutically acceptable salt dissolved in water. Aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is obvious that all the products participating in the compositions according to the invention must be pure and nontoxic in the amounts used.

The compositions can contain at least 0.01% of therapeutically active product. The amount of active product in a composition is such as to enable an appropriate dosage to be prescribed. Preferably, the compositions are prepared in such a way that a single dose contains from 0.01 to 1,000 mg approximately of active product for parenteral administration.

The therapeutic treatment may be carried out conjointly with other therapeutic treatments including antineoplastic medicinal products, monoclonal antibodies, immunological therapies or radiotherapies or biological-response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents such as nitrogen mustards, for instance mechloretamine, cyclophosphamide, melphalan and chlorambucil, alkyl sulphonates such as busulphan, nitrosoureas such as carmustine, lomusine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products such as vinca alkaloids, for instance vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for example cisplatin, substituted ureas such as hydroxyurea, methylhydrazine derivatives such as procarbazine, adrenocoticoid suppressants such as mitotane and aminoglutethymide, hormones and antagonists such as adrenocorticosteroids such as prednisone, progestins such as hydroxyprogesterone caproate, methoxyprogesterone acetate and megestrol acetate, oestrogens such as diethylstilboestrol and ethinyloestradiol, anti-oestrogens such as tamoxifen, and androgens such as testosterone propionate and fluoxymesterone.

The doses used for implementing the methods according to the invention are those which permit a prophylactic treatment or a maximum therapeutic response. The doses vary according to the form of administration, the particular product selected and the features distinctive to the subject to be treated. In general, the doses are those which are therapeutically effective for the treatment of disorders due to an abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly higher doses will be administered until an optimum effect is obtained. For other patients, it may be necessary to administer maintenance doses 1 to 8 times a day, preferably 1 to 4 times, according to the physiological requirements of the patient in question. For some patients, it is also possible for it to be necessary to use only one to two daily administrations.

In humans, the doses are generally between 0.01 and 200 mg/kg. Intraperitoneally, the doses will generally be between 0.1 and 100 mg/kg, and preferably between 0.5 and 50 mg/kg, and still more specifically between 1 and 10 mg/kg. Intravenously, the doses are generally between 0.1 and 50 mg/kg, and preferably between 0.1 and 5 mg/kg, and still more specifically between 1 and 2 mg/kg. It is understood that, in order to choose the most suitable dosage, account should be taken of the administration route, the patient's weight, general state of health and age and all factors which may influence the efficacy of the treatment.

The following example illustrates a composition according to the invention.

EXAMPLE 40 mg of the product obtained in Example 1 are dissolved in 1 cm³ of Emulphor EL 620 and 1 cm³ of ethanol and the solution is then diluted by addition of 18 cm³ of physiological serum.

The composition is administered via a drip for one hour by introduction into physiological solution.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:
1. Process for the preparation of products of formula:

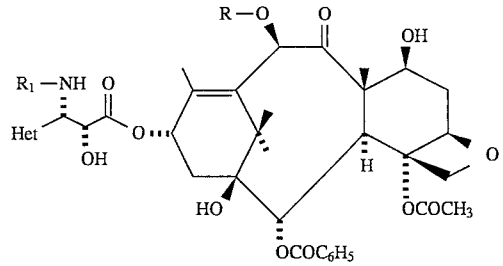

in which:

R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or heterocyclyl radical, and Het represents an optionally substituted aromatic heterocyclyl radical having 5 members and containing at least one heteroatom, which are identical or different, selected from nitrogen, oxygen and sulphur, comprising treating a product of formula:

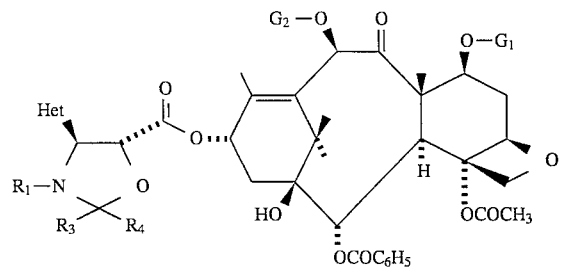

in which Het and $R_1$ are defined as above, $G_1$ represents a protective group of the hydroxyl functional group, $G_2$ represents an acetyl radical or a protective group of the hydroxyl functional group, $R_3$ represents a hydrogen atom or an alkoxy radical or an optionally substituted aryl radical and $R_4$ represents a hydrogen atom, in acid medium to produce a product of formula:

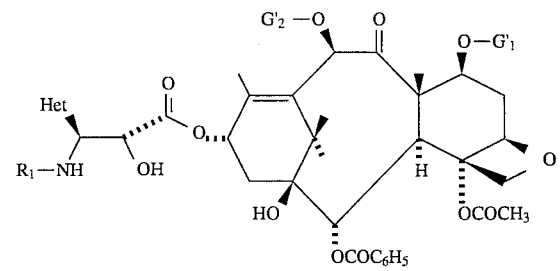

in which Het and $R_1$ are defined as above, $G'_1$ represents a hydrogen atom or a protective group of the hydroxyl functional group and $G'_2$ represents a hydrogen atom or an acetyl radical or a protective group of the hydroxyl functional group, and then, optionally, the $G'_1$ and $G'_2$ protective groups are replaced by hydrogen atoms and the product thus obtained is isolated.

2. Process for the preparation according to claim 1 of products for which

R represents a hydrogen atom or an acetyl radical, $R_1$ represents a benzoyl radical or a radical $R_2$—O—CO in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by at least one substituent, which are identical or different, selected from the halogen atoms and the hydroxyl radical, alkoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, nitro radical, carboxyl radical or alkoxycarbonyl radical, the alkyl part of which contains 1 to 4 carbon atoms, or a phenyl radical, optionally substituted by at least one radical, which are identical or different, selected from the alkyl radicals containing 1 to 4 carbon atoms or the alkoxy radicals containing 1 to 4 carbon atoms, or a saturated or unsaturated nitrogen-containing heterocyclyl radical containing 5 or 6 members, optionally substituted by at least one alkyl radical containing 1 to 4 carbon atoms, the cycloalkyl, cycloalkenyl or bicycloalkyl radicals may optionally be substituted by at least one alkyl radical containing 1 to 4 carbon atoms, and Het represents an aromatic heterocyclic radical having 5 members and containing at least one atom, which are identical or different, selected from the nitrogen, oxygen or sulphur atoms, such as thiophene, thiazole, furan, pyrrole, imidazole, isoxazole or pyrazole, optionally substituted by at least one substituent, which are identical or different, selected from the halogen atoms including fluorine and chlorine and the alkyl, containing 1 to 4 carbon atoms, aryl, containing 6 to 10 carbon atoms, alkoxy, containing 1 to 4 carbon atoms, aryloxy, containing 6 to 10 carbon atoms, amino, alkylamino, containing 1 to 4 carbon atoms, dialkylamino, each alkyl part of which contains 1 to 4 carbon atoms, acylamino, the acyl part of which contains 1 to 4 carbon atoms, alkoxycarbonylamino, containing 1 to 4 carbon atoms, acyl, containing 1 to 4 carbon atoms, arylcarbonyl, the aryl part of which contains 6 to 10 carbon atoms, cyano, nitro, hydroxyl, carboxyl, carbamoyl, alkylcarbamoyl, the alkyl part of which contains 1 to 4 carbon atoms, dialkylcarbamoyl, each alkyl part of which contains 1 to 4 carbon atoms, or alkoxycarbonyl, the alkoxy part of which contains 1 to 4 carbon atoms, radicals.

3. Process for the preparation according to claim 1 of products of which R represents a hydrogen atom or an acetyl radical, $R_1$ represents a benzoyl radical or a radical $R_2$—O—CO— in which $R_2$ represents a t-butyl radical and Het represents a 2- or 3-thienyl or 2-or 3-furyl radical.

4. Process according to claim 1, wherein the acid treatment is carried out by means of an inorganic or organic acid in an organic solvent at a temperature between −10° and 60° C.

5. Process according to claim 4, wherein the acid is selected from hydrochloric, sulphuric, acetic, methanesulphonic, trifluoromethanesulphonic and p-toluenesulphonic acids, used alone or as a mixture.

6. Process according to claim 4, wherein the solvent is selected from alcohols, ethers, esters, halogenated aliphatic hydrocarbons, aromatic hydrocarbons and nitriles.

7. Process according to claim 1, wherein the protective groups of the hydroxyl functional groups are selected from the 2,2,2-trichloroethoxycarbonyl, 2-(2-(trichloromethyl)propoxy)carbonyl, trialkylsilyl, dialkylarylsilyl, alkyldiarylsilyl and triarylsilyl radicals in which the alkyl radicals contain 1 to 4 carbon atoms and the aryl radicals are phenyl radicals.

8. Process according to claim 7, wherein, when $G_1$ and/or $G_2$ represent a silylated radical, their replacement by hydrogen atoms is carried out simultaneously with the replacement of the protective group of the side chain by treatment in acid medium.

9. Process according to claim 7, wherein, when $G'_1$ and/or $G'_2$ represent a 2,2,2-trichloroethoxycarbonyl or 2-(2-(trichloromethyl)propoxy)carbonyl radical, their replacement by a hydrogen atom is carried out with zinc, optionally in combination with copper, in the presence of acetic acid at a temperature between 20° and 60° C. or else by means of an inorganic or organic acid in solution in an aliphatic alcohol or in an aliphatic ester in the presence of zinc, optionally in combination with copper.

10. Process according to one of claim 1, wherein a product of formula:

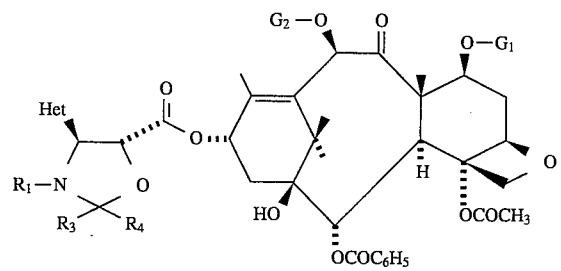

in which Het and $R_1$ are defined as in one of claims 1, 2 or 3, $G_1$ represents a protective group of the hydroxyl functional group, $G_2$ represents an acetyl radical or a protective group of the hydroxyl functional group, $R_3$ and $R_4$, which are identical or different, represent an alkyl radical containing 1 to 4 carbon atoms or an aralkyl radical, the alkyl part of which contains 1 to 4 carbon atoms, or an aryl radical, or else $R_3$ represents a trihalomethyl radical or a phenyl radical substituted by a trihalomethyl radical and $R_4$ represents a hydrogen atom, or else $R_3$ and $R_4$ form, together with the carbon atom to which they are bonded, a ring having 4 to 7 members, is treated in acid medium to produce a product of formula:

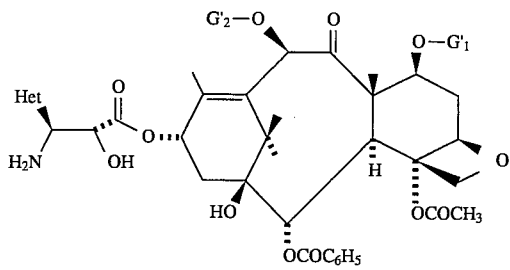

in which Het is defined as in one of claims 1, 2 or 3, $G'_1$ represents a hydrogen atom or a protective group of the hydroxyl functional group and $G'_2$ represents an acetyl radical or a protective group of the hydroxyl functional group, which is acylated by means of benzoyl chloride or of a reactive derivative of formula:

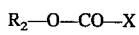

$$R_2-O-CO-X$$

in which $R_2$ is defined as in one of claims 1, 2 or 3 and X represents a halogen atom or an —O—$R_2$ or —O—CO—O—$R_2$ residue, to produce a product of formula:

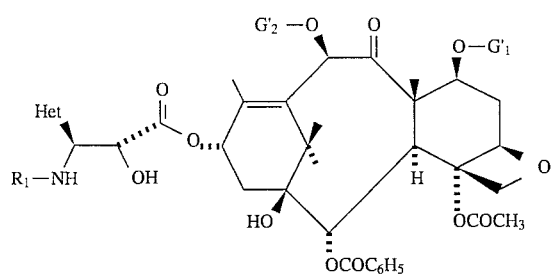

in which Het, $R_1$, $G'_1$ and $G'_2$ are defined as above, the $G'_1$ and $G'_2$ protective groups are then replaced, if necessary, by hydrogen atoms, and the product obtained is isolated.

11. Process according to claim 10, wherein the acid treatment is carried out by means of an inorganic or organic acid in an organic solvent at a temperature between $-10°$ and $60°$ C.

12. Process according to claim 11, wherein the acid is selected from hydrochloric, sulphuric, acetic, methanesulphonic, trifluoromethanesulphonic, p-toluenesulphonic and formic acids, used alone or as a mixture.

13. Process according to claim 11, wherein the solvent is selected from alcohols, ethers, esters, halogenated aliphatic hydrocarbons, aromatic hydrocarbons and nitriles.

14. Process according to claim 10, wherein the acylation is carried out in an inert organic solvent in the presence of an inorganic or organic base.

15. Process according to claim 14, wherein the inert organic solvent is selected from esters and halogenated aliphatic hydrocarbons.

16. Process according to claim 13, wherein the reaction is carried out at a temperature between $0°$ and $50°$ C.

17. Process according to claim 10, wherein the replacement by hydrogen atoms of the $G'_1$ and optionally $G'_2$ protective groups, when they represent a 2,2,2-trichloroethoxycarbonyl or 2-(2-(trichloromethyl)propoxy)carbonyl radical, is carried out with zinc, optionally in combination with copper, in the presence of acetic acid at a temperature between $30°$ and $60°$ C. or by means of an inorganic or organic acid in solution in an aliphatic alcohol containing 1 to 3 carbon atoms or in an aliphatic ester in the presence of zinc, optionally in combination with copper.

18. Process for the preparation of a product of formula:

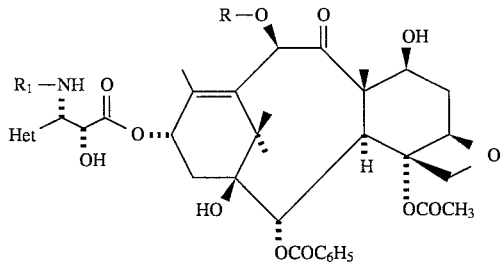

in which:

R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or heterocyclyl radical, and Het represents an optionally substituted aromatic heterocyclyl radical having 5 members and containing at least one identical or different heteroatom selected from nitrogen, oxygen and sulphur, comprising esterifying protected 10-deacetylbaccatin III or baccatin III of formula:

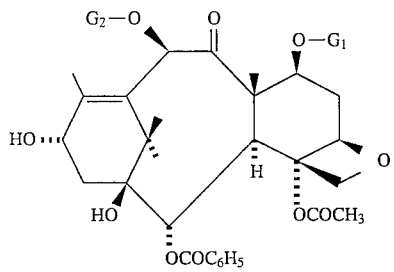

in which $G_1$ represents a protective group of the hydroxyl functional group and $G_2$ represents an acetyl radical or a protective group of the hydroxyl functional group, by means of an acid of formula:

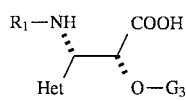

in which Het and $R_1$ are defined as in claim 1, and $G_3$ represents a protective group of the hydroxyl functional group, or of an activated derivative of this acid, to produce a product of formula:

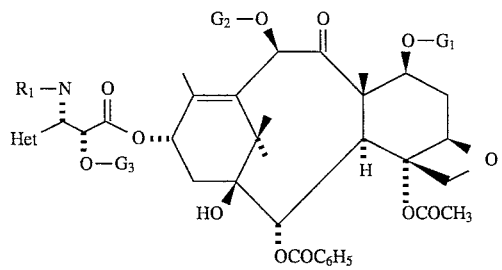

in which Het, $R_1$, $G_1$, $G_2$ and $G_3$ are defined as above, the $G_1$, $G_2$ and $G_3$ protective groups of which are replaced by hydrogen atoms, and the product obtained is isolated.

19. Process for the preparation according to claim 18 of products wherein

R represents a hydrogen atom or an acetyl radical, $R_1$ represents a benzoyl radical or a radical $R_2$—O—CO in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by at least one substituent, which are identical or different, selected from the halogen atoms and the hydroxyl radical, alkoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, nitro radical, carboxyl radical or alkoxycarbonyl radical, the alkyl part of which contains 1 to 4 carbon atoms, or a phenyl radical, optionally substituted by at least one radical, which are identical or different, selected from the alkyl radicals containing 1 to 4 carbon atoms or the alkoxy radicals containing 1 to 4 carbon atoms, or a saturated or unsaturated nitrogen-containing heterocyclyl radical containing 5 or 6 members, optionally substituted by at least one alkyl radical containing 1 to 4 carbon atoms, the cycloalkyl, cycloalkenyl or bicycloalkyl radicals optionally be substituted by at least one alkyl radical containing 1 to 4 carbon atoms, and Het represents an aromatic heterocyclic radical having 5 members and containing at least one atom, which are identical or different, selected from the nitrogen, oxygen or sulphur atoms, including thiophene, thiazole, furan, pyrrole, imidazole, isoxazole or pyrazole, optionally substituted by at least one substituent, which are identical or different, selected from the halogen atoms including fluorine and chlorine and the alkyl, containing 1 to 4 carbon atoms, aryl, containing 6 to 10 carbon atoms, alkoxy, containing 1 to 4 carbon atoms, aryloxy, containing 6 to 10 carbon atoms, amino, alkylamino, containing 1 to 4 carbon atoms, dialkylamino, each alkyl part of which contains 1 to 4 carbon atoms, acylamino, the acyl part of which contains 1 to 4 carbon atoms, alkoxycarbonylamino, containing 1 to 4 carbon atoms, acyl, containing 1 to 4 carbon atoms, arylcarbonyl, the aryl part of which contains 6 to 10 carbon atoms, cyano, nitro, hydroxyl, carboxyl, carbamoyl, alkylcarbamoyl, the alkyl part of which contains 1 to 4 carbon atoms, dialkylcarbamoyl, each alkyl part of which contains 1 to 4 carbon atoms, or alkoxycarbonyl, the alkoxy part of which contains 1 to 4 carbon atoms, radicals.

20. Process for the preparation according to claim 18 of products wherein R represents a hydrogen atom or an acetyl radical, $R_1$ represents a benzoyl radical or a radical $R_2$—O—CO— in which $R_2$ represents a t-butyl radical and Het represents a 3-thienyl or 3-furyl radical.

21. Process according to claim 18, wherein the esterification is carried out by means of free acid, the reaction being carried out in the presence of a condensation agent selected from carbodiimides and reactive carbonates and of an activating agent selected from aminopyridines in an organic solvent selected from ethers, ketones, esters, nitriles, aliphatic hydrocarbons, halogenated aliphatic hydrocarbons and aromatic hydrocarbons at a temperature between —10° and 90° C.

22. Process according to claim 18, wherein the esterification by means of the anhydride is carried out in the presence of an activating agent selected from aminopyridines in an organic solvent selected from ethers, esters, ketones, nitriles, aliphatic hydrocarbons, halogenated aliphatic hydrocarbons and aromatic hydrocarbons at a temperature between 0° and 90° C.

23. Process according to claim 18, wherein the esterification is carried out by means of a halide or of an anhydride with an aliphatic or aromatic acid, optionally prepared in situ, the reaction being carried out in the presence of a base selected from tertiary aliphatic amines in an organic solvent selected from ethers, esters, ketones, nitriles, aliphatic hydrocarbons, halogenated aliphatic hydrocarbons and aromatic hydrocarbons at a temperature between 0° and 80° C.

24. Process according to claim 18, wherein the replacement of the $G_1$, $G_2$ and $G_3$ protective groups by hydrogen atoms is carried out by treatment With zinc, optionally in combination with copper, in the presence of acetic acid at a temperature between 30° and 60° C. or by means of an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc, optionally in combination with some copper, when $G_1$, $G_2$ and/or $G_3$ represent a 2,2,2-trichloroethoxycarbonyl or 2-(2(trichloromethyl)propoxy)carbonyl radical, or by treatment in acid medium such as for example hydrochloric acid in solution in an aliphatic alcohol containing 1 to 3 carbon atoms including methanol, ethanol, propanol and isopropanol or aqueous hydrofluoric acid at a temperature between 0° and 40° C. when $G_1$, $G_2$ and/or $G_3$ represent a silylated radical.

25. Process according to claim 18, characterized in that, when $G_3$ represents a —$CH_2$—Ph radical, the replacement is first carried out of the $G_1$ and $G_2$ groups by hydrogen atoms under the conditions of claim 24 before replacing the $G_3$ group by hydrogenolysis.

* * * * *